(12) United States Patent
Velasquez et al.

(10) Patent No.: US 10,294,186 B2
(45) Date of Patent: May 21, 2019

(54) CATALYSTS FOR THE PRODUCTION OF ACRYLIC ACID OR ITS DERIVATIVES

(71) Applicant: The Procter & Gamble Company, Cincinnati, OH (US)

(72) Inventors: Juan Esteban Velasquez, Cincinnati, OH (US); Janette Villalobos Lingoes, Cincinnati, OH (US); Dimitris Ioannis Collias, Mason, OH (US); Jane Ellen Godlewski, Loveland, OH (US); Marc Andrew Mamak, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 582 days.

(21) Appl. No.: 13/840,192

(22) Filed: Mar. 15, 2013

(65) Prior Publication Data

US 2013/0274095 A1     Oct. 17, 2013

Related U.S. Application Data

(63) Continuation-in-part of application No. 13/760,444, filed on Feb. 6, 2013, now Pat. No. 10,106,484.

(60) Provisional application No. 61/623,054, filed on Apr. 11, 2012.

(51) Int. Cl.
| | |
|---|---|
| *B01J 27/18* | (2006.01) |
| *C07C 51/48* | (2006.01) |
| *B01J 27/187* | (2006.01) |
| *B01J 27/25* | (2006.01) |
| *C07C 51/377* | (2006.01) |
| *C07C 51/09* | (2006.01) |
| *C07C 57/04* | (2006.01) |
| *A61F 13/534* | (2006.01) |
| *C08F 2/10* | (2006.01) |
| *B01J 27/16* | (2006.01) |
| *B01J 27/185* | (2006.01) |
| *B01J 27/186* | (2006.01) |
| *B01J 27/188* | (2006.01) |
| *B01J 27/195* | (2006.01) |
| *B01J 27/198* | (2006.01) |
| *B01J 35/02* | (2006.01) |
| *B01J 37/00* | (2006.01) |
| *B01J 37/04* | (2006.01) |
| *B01J 37/08* | (2006.01) |
| *C07C 51/44* | (2006.01) |
| *A61F 13/53* | (2006.01) |

(52) U.S. Cl.
CPC .......... *C07C 51/48* (2013.01); *A61F 13/534* (2013.01); *B01J 27/16* (2013.01); *B01J 27/1806* (2013.01); *B01J 27/186* (2013.01); *B01J 27/187* (2013.01); *B01J 27/188* (2013.01); *B01J 27/1811* (2013.01); *B01J 27/1817* (2013.01); *B01J 27/1853* (2013.01); *B01J 27/1856* (2013.01); *B01J 27/195* (2013.01); *B01J 27/198* (2013.01); *B01J 27/25* (2013.01); *B01J 35/023* (2013.01); *B01J 37/0036* (2013.01); *B01J 37/04* (2013.01); *B01J 37/08* (2013.01); *C07C 51/09* (2013.01); *C07C 51/377* (2013.01); *C07C 51/44* (2013.01); *C07C 57/04* (2013.01); *C08F 2/10* (2013.01); *A61F 13/53* (2013.01); *A61F 2013/530489* (2013.01); *A61F 2013/530496* (2013.01)

(58) Field of Classification Search
None
See application file for complete search history.

(56) References Cited

U.S. PATENT DOCUMENTS

| | | | |
|---|---|---|---|
| 2,444,538 A | 7/1948 | Seymour et al. | |
| 2,859,240 A * | 11/1958 | Holmen | C07C 51/377 |
| | | | 502/208 |
| 3,781,222 A | 12/1973 | Weisang et al. | |
| 4,028,424 A * | 6/1977 | Yoshida | C07C 29/38 |
| | | | 568/879 |
| 4,158,741 A * | 6/1979 | Goi | C07C 51/09 |
| | | | 562/599 |
| 4,695,661 A | 9/1987 | Homann et al. | |
| 4,786,756 A | 11/1988 | Paparizos et al. | |
| 5,616,817 A * | 4/1997 | Schuster | C07C 29/60 |
| | | | 568/861 |
| 7,683,220 B2 | 3/2010 | Matsunami et al. | |

FOREIGN PATENT DOCUMENTS

| | | | |
|---|---|---|---|
| CN | 200910054519.7 | 7/2009 | |
| DE | 1062696 B | 8/1959 | |
| GB | 1489832 | 10/1977 | |
| GB | 2086892 | 5/1982 | |
| WO | WO 9718892 A1 * | 5/1997 | ............ B01J 21/06 |

OTHER PUBLICATIONS

International Search Report and Written Opinion for 12734 dated Oct. 8, 2013.
International Search Report and Written Opinion for 12811 dated Apr. 11, 2013.
Gunter et al.; J. Catalysis 148:252-260, 1994.
Hong et al.; Appl. Catal. A: General 396:194-200, 2011.
Kirk-Othmer Encylcopedia of Chemical Technology, vol. 1, pp. 324-369, 5$^{th}$ Ed., John Wiley & Sons, Inc., 2004.
Tam et al.; Ind. Eng. Chem. Res: 38:3873-3877, 1999.

\* cited by examiner

*Primary Examiner* — Melissa S Swain
(74) *Attorney, Agent, or Firm* — Jason J Camp; James T Fondriest

(57) ABSTRACT

Catalysts for dehydrating hydroxypropionic acid, hydroxypropionic acid derivatives, or mixtures thereof to acrylic acid, acrylic acid derivatives, or mixtures thereof with high yield and selectivity, short residence time, and without significant conversion to undesired side products, such as, for example, acetaldehyde, propionic acid, and acetic acid, are provided. The catalysts are mixed protonated monophosphates. Methods of preparing the catalysts are also provided.

1 Claim, No Drawings

CATALYSTS FOR THE PRODUCTION OF ACRYLIC ACID OR ITS DERIVATIVES

FIELD OF THE INVENTION

The present invention generally relates to catalysts useful for the conversion of hydroxypropionic acid, hydroxypropionic acid derivatives, or mixtures thereof to acrylic acid, acrylic acid derivatives, or mixtures thereof. More specifically, the invention relates to catalysts useful for the dehydration of hydroxypropionic acid, hydroxypropionic acid derivatives, or mixtures thereof to acrylic acid, acrylic acid derivatives, or mixtures thereof with high yield and selectivity to acrylic acid, acrylic acid derivatives, or mixtures thereof, short residence time, and without significant conversion of the hydroxypropionic acid, hydroxypropionic acid derivatives, or mixtures thereof to undesired side products, such as, for example, acetaldehyde, propionic acid, acetic acid, 2,3-pentanedione, carbon dioxide, and carbon monoxide.

BACKGROUND OF THE INVENTION

Acrylic acid, acrylic acid derivatives, or mixtures thereof have a variety of industrial uses, typically consumed in the form of polymers. In turn, these polymers are commonly used in the manufacture of, among other things, adhesives, binders, coatings, paints, polishes, detergents, flocculants, dispersants, thixotropic agents, sequestrants, and superabsorbent polymers, which are used in disposable absorbent articles, including diapers and hygienic products, for example. Acrylic acid is commonly made from petroleum sources. For example, acrylic acid has long been prepared by catalytic oxidation of propylene. These and other methods of making acrylic acid from petroleum sources are described in the Kirk-Othmer Encyclopedia of Chemical Technology, Vol. 1, pgs. 342-369 ($5^{th}$ Ed., John Wiley & Sons, Inc., 2004). Petroleum-based acrylic acid contributes to greenhouse emissions due to its high petroleum derived carbon content. Furthermore, petroleum is a non-renewable material, as it takes hundreds of thousands of years to form naturally and only a short time to consume. As petrochemical resources become increasingly scarce, more expensive, and subject to regulations for $CO_2$ emissions, there exists a growing need for bio-based acrylic acid, acrylic acid derivatives, or mixtures thereof that can serve as an alternative to petroleum-based acrylic acid, acrylic acid derivatives, or mixtures thereof.

Many attempts have been made over the last 40 to 50 years to make bio-based acrylic acid, acrylic acid derivatives, or mixtures thereof from non-petroleum sources, such as lactic acid (also known as 2-hydroxypropionic acid), 3-hydroxypropionic acid, glycerin, carbon monoxide and ethylene oxide, carbon dioxide and ethylene, and crotonic acid. From these non-petroleum sources, only lactic acid is produced today in high yield from sugar (≥90% of theoretical yield, or equivalently, ≥0.9 g of lactic acid per g of sugar) and purity, and economics which could support producing acrylic acid at a cost competitive to petroleum-based acrylic acid. As such, lactic acid or lactate presents a real opportunity of serving as a feedstock for bio-based acrylic acid, acrylic acid derivatives, or mixtures thereof. Also, 3-hydroxypropionic acid is expected to be produced at commercial scale in a few years, and as such, 3-hydropropionic acid will present another real opportunity of serving as feedstock for bio-based acrylic acid, acrylic acid derivatives, or mixtures thereof. Sulfate salts; phosphate salts; mixtures of sulfate and phosphate salts; bases; zeolites or modified zeolites; metal oxides or modified metal oxides; and supercritical water are the main catalysts which have been used to dehydrate lactic acid or lactate to acrylic acid, acrylic acid derivatives, or mixtures thereof in the past with varying success.

For example, U.S. Pat. No. 4,786,756 (issued in 1988), describes the vapor phase dehydration of lactic acid or ammonium lactate to acrylic acid using aluminum phosphate ($AlPO_4$) treated with an aqueous inorganic base as a catalyst. As an example, the '756 patent discloses a maximum yield of acrylic acid of 43.3% when lactic acid was fed into the reactor at approximately atmospheric pressure, and a respective yield of 61.1% when ammonium lactate was fed into the reactor. In both examples, acetaldehyde was produced at yields of 34.7% and 11.9%, respectively, and other side products were also present in large quantities, such as, propionic acid, CO, and $CO_2$. Omission of the base treatment caused increased amounts of the side products.

Another example is Hong et al. (2011) *Appl. Catal. A: General* 396:194-200, who developed and tested composite catalysts made with $Ca_3(PO_4)_2$ and $Ca_2(P_2O_7)$ salts with a slurry-mixing method. The catalyst with the highest yield of acrylic acid from methyl lactate was the 50%-50% (by weight) catalyst. It yielded 68% acrylic acid, about 5% methyl acrylate, and about 14% acetaldehyde at 390° C. The same catalyst achieved 54% yield of acrylic acid, 14% yield of acetaldehyde, and 14% yield of propionic acid from lactic acid.

Prof. D. Miller's group at Michigan State University (MSU) published many papers on the dehydration of lactic acid or lactic acid esters to acrylic acid and 2,3-pentanedione, such as, Gunter et al. (1994) *J. Catalysis* 148: 252-260; and Tam et al. (1999) *Ind. Eng. Chem. Res.* 38:3873-3877. The best acrylic acid yields reported by the group were about 33% when lactic acid was dehydrated at 350° C. over low surface area and pore volume silica impregnated with NaOH. In the same experiment, the acetaldehyde yield was 14.7% and the propionic acid yield was 4.1%. Examples of other catalysts tested by the group were $Na_2SO_4$, NaCl, $Na_3PO_4$, $NaNO_3$, $Na_2SiO_3$, $Na_4P_2O_7$, $NaH_2PO_4$, $Na_2HPO_4$, $Na_2HAsO_4$, $NaC_3H_5O_3$, NaOH, CsCl, $Cs_2SO_4$, KOH, CsOH, and LiOH. In all cases, the above referenced catalysts were tested as individual components, not in mixtures. Finally, the group suggested that the yield to acrylic acid is improved and the yield to the side products is suppressed when the surface area of the silica support is low, reaction temperature is high, reaction pressure is low, and residence time of the reactants in the catalyst bed is short.

Finally, the Chinese patent application 200910054519.7 discloses the use of ZSM-5 molecular sieves modified with aqueous alkali (such as, $NH_3$, NaOH, and $Na_2CO_3$) or a phosphoric acid salt (such as, $NaH_2PO_4$, $Na_2HPO_4$, $LiH_2PO_4$, $LaPO_4$, etc.). The best yield of acrylic acid achieved in the dehydration of lactic acid was 83.9%, however that yield came at very long residence times.

Therefore, the manufacture of acrylic acid, acrylic acid derivatives, or mixtures thereof from lactic acid or lactate by processes, such as those described in the literature noted above, has demonstrated: 1) yields of acrylic acid, acrylic acid derivatives, or mixtures thereof not exceeding 70%; 2) low selectivities of acrylic acid, acrylic acid derivatives, or mixtures thereof, i.e., significant amounts of undesired side products, such as, acetaldehyde, 2,3-pentanedione, propionic acid, CO, and $CO_2$; 3) long residence times in the catalyst beds; and 4) catalyst deactivation in short time on stream (TOS). The side products can deposit onto the catalyst resulting in fouling, and premature and rapid deactivation of the catalyst. Further, once deposited, these side products can catalyze other undesired reactions, such as polymerization reactions. Aside from depositing on the catalysts, these side products, even when present in only small amounts, impose additional costs in processing acrylic acid (when present in the reaction product effluent) in the manufacture of superabsorbent polymers (SAP), for example. These deficiencies of the prior art processes and catalysts render them commercially non-viable.

Accordingly, there is a need for catalysts and methods for the dehydration of hydroxypropionic acid, hydroxypropionic acid derivatives, or mixtures thereof to acrylic acid, acrylic acid derivatives, or mixtures thereof, with high yield, selectivity, and efficiency (i.e., short residence time), and high longevity catalysts.

SUMMARY OF THE INVENTION

A catalyst for dehydrating hydroxypropionic acid, hydroxypropionic acid derivatives, or mixtures thereof to acrylic acid, acrylic acid derivatives, or mixtures thereof is provided. In one embodiment of the present invention, the catalyst includes: (a) monohydrogen monophosphate described by formula (I)

$$[HPO_4]^{2-} \quad (I),$$

(b) dihydrogen monophosphate anions described by formula (II):

$$[H_2PO_4]^{-} \quad (II),$$

and (c) at least two different cations, wherein the catalyst is essentially neutrally charged; and further, wherein the molar ratio of said monohydrogen monophosphate anion to said dihydrogen monophosphate anion in said catalyst is between about 0.1 and about 10.

In another embodiment of the present invention, the catalyst includes the monophosphate salts described by both formulae (III) and (IV):

$$M^{II}HPO_4 \quad (III),$$

$$M^{I}H_2PO_4 \quad (IV), \text{ and}$$

wherein $M^I$ is a monovalent cation and $M^{II}$ is a divalent cation.

In yet another embodiment of the present invention, the catalyst includes a monophosphate salt described by formula (V):

$$M^{II}_{2-x}M^{I}_{x}H_xH_x(HPO_4)_2 \quad (V),$$

wherein $M^I$ is a monovalent cation and $M^{II}$ is a divalent cation; and wherein x is greater than about 0.2 and smaller than about 1.8.

In another embodiment of the present invention, there is provided a method of preparing the catalyst. The method includes mixing at least two phosphorus-containing compounds, wherein each said compound is described by one of formulae (VI) to (XXV), or any of the hydrated forms of said formulae:

$$M^{I}_{a}(H_{3-a}PO_4) \quad (VI)$$

$$M^{II}_{a}(H_{3-a}PO_4)_2 \quad (VII)$$

$$M^{III}_{a}(H_{3-a}PO_4)_3 \quad (VIII)$$

$$M^{IV}_{a}(H_{3-a}PO_4)_4 \quad (IX)$$

$$M^{II}_{b}(OH)_c(PO_4)_d \quad (X)$$

$$M^{III}_{e}(OH)_f(PO_4)_g \quad (XI)$$

$$M^{II}M^{I}PO_4 \quad (XII)$$

$$M^{III}M^{I}_{3}(PO_4)_2 \quad (XIII)$$

$$M^{IV}_{2}M^{I}(PO_4)_3 \quad (XIV)$$

$$M^{I}_{h}H_{4-h}P_2O_7 \quad (XV)$$

$$M^{II}_{i}H_{(4-2i)}P_2O_7 \quad (XVI)$$

$$M^{IV}P_2O_7 \quad (XVII)$$

$$M^{III}M^{I}P_2O_7 \quad (XVIII)$$

$$M^{I}H_j(PO_3)_{(1+j)} \quad (XIX)$$

$$M^{II}H_j(PO_3)_{(2+j)} \quad (XX)$$

$$M^{III}H_j(PO_3)_{(3+j)} \quad (XXI)$$

$$M^{IV}H_j(PO_3)_{(4+j)} \quad (XXII)$$

$$M^{II}_{k}M^{I}_{l}(PO_3)_r \quad (XXIII)$$

$$M^{III}_{q}M^{I}_{p}(PO_3)_s \quad (XXIV)$$

$$P_2O_5 \quad (XXV)$$

wherein $M^I$ is a monovalent cation; wherein $M^{II}$ is a divalent cation; wherein $M^{III}$ is a trivalent cation; wherein $M^{IV}$ is a tetravalent cation; wherein a is 0, 1, 2, or 3; wherein h is 0, 1, 2, 3, or 4; wherein i is 0, 1, or 2; wherein j is 0 or any positive integer; and wherein b, c, d, e, f, g, k, l, m, n, p and q are any positive integers, such that the equations: $2b=c+3d$, $3e=f+3g$, $r=2k+l$, and $s=3q+p$ are satisfied.

In yet another embodiment of the present invention, there is provided a method of preparing the catalyst. The method includes mixing and heating: (a) at least one phosphorus-containing compound, wherein each said compound is described by one of formulae (VI) to (XXV), or any of the hydrated forms of said formulae:

$$M^{I}_{a}(H_{3-a}PO_4) \quad (VI)$$

$$M^{II}_{a}(H_{3-a}PO_4)_2 \quad (VII)$$

$$M^{III}_{a}(H_{3-a}PO_4)_3 \quad (VIII)$$

$$M^{IV}_{a}(H_{3-a}PO_4)_4 \quad (IX)$$

$$M^{II}_{b}(OH)_c(PO_4)_d \quad (X)$$

$$M^{III}_{e}(OH)_f(PO_4)_g \quad (XI)$$

$$M^{II}M^{I}PO_4 \quad (XII)$$

$$M^{III}M^{I}_{3}(PO_4)_2 \quad (XIII)$$

$$M^{IV}_{2}M^{I}(PO_4)_3 \quad (XIV)$$

$$M^{I}_{h}H_{4-h}P_2O_7 \quad (XV)$$

$$M^{II}_{i}H_{(4-2i)}P_2O_7 \quad (XVI)$$

$$M^{IV}P_2O_7 \quad (XVII)$$

$$M^{III}M^{I}P_2O_7 \quad (XVIII)$$

$$M^{I}H_j(PO_3)_{(1+j)} \quad (XIX)$$

$$M^{II}H_j(PO_3)_{(2+j)} \quad (XX)$$

$M^{III}H_j(PO_3)_{(3+j)}$ (XXI)

$M^{IV}H_j(PO_3)_{(4+j)}$ (XXII)

$M^{II}_k M^I_l (PO_3)_r$ (XXIII)

$M^{III}_q M^I_p (PO_3)_s$ (XXIV)

$P_2O_5$ (XXV)

wherein $M^I$ is a monovalent cation; wherein $M^{II}$ is a divalent cation; wherein $M^{III}$ is a trivalent cation; wherein $M^{IV}$ is a tetravalent cation; wherein a is 0, 1, 2, or 3; wherein h is 0, 1, 2, 3, or 4; wherein i is 0, 1, or 2; wherein j is 0 or any positive integer; and wherein b, c, d, e, f, g, k, l, m, n, p and q are any positive integers, such that the equations: $2b=c+3d$, $3e=f+3g$, $r=2k+l$, and $s=3q+p$ are satisfied; and (b) at least one non-phosphorus-containing compound selected from the group consisting of nitrate salts, carbonate salts, acetate salts, metal oxides, chloride salts, sulfate salts, and metal hydroxides, wherein each said compound is described by one of formulae (XXVI) to (L), or any of the hydrated forms of said formulae:

$M^I NO_3$ (XXVI)

$M^{II}(NO_3)_2$ (XXVII)

$M^{III}(NO_3)_3$ (XXVIII)

$M^I_2 CO_3$ (XXIX)

$M^{II} CO_3$ (XXX)

$M^{III}_2(CO_3)_3$ (XXXI)

$(CH_3COO)M^I$ (XXXII)

$(CH_3COO)_2 M^{II}$ (XXXIII)

$(CH_3COO)_3 M^{III}$ (XXXIV)

$(CH_3COO)_4 M^{IV}$ (XXXV)

$M^I_2 O$ (XXXVI)

$M^{II} O$ (XXXVII)

$M^{III}_2 O_3$ (XXXVIII)

$M^{IV} O_2$ (XXXIX)

$M^I Cl$ (XL)

$M^{II} Cl_2$ (XLI)

$M^{III} Cl_3$ (XLII)

$M^{IV} Cl_4$ (XLIII)

$M^I_2 SO_4$ (XLIV)

$M^{II} SO_4$ (XLV)

$M^{III}_2(SO_4)_3$ (XLVI)

$M^{IV}(SO_4)_2$ (XLVII)

$M^I OH$ (XLVIII)

$M^{II}(OH)_2$ (XLIX)

$M^{III}(OH)_3$ (L)

In another embodiment of the present invention, there is provided a method for preparing the catalyst. The method includes contacting: (a) a gaseous mixture comprising water, with (b) a mixture of compounds comprising at least one condensed phosphate anion selected from the group consisting of formulae (LI) to (LIII), $[P_n O_{3n+1}]^{(n+2)-}$ (LI)

$[P_n O_{3n}]^{n-}$ (LII)

$[P_{(2m+n)} O_{(5m+3n)}]^{n-}$ (LIII)

wherein n is at least 2; wherein m is at least 1; wherein, said mixture of compounds is essentially neutrally charged; and further, wherein the molar ratio of phosphorus to said at least one monovalent cation and at least one polyvalent cation in said catalyst is between about 0.7 and about 1.7.

In another embodiment of the present invention, a method of preparing a catalyst is provided including combining $BaHPO_4$ and $KH_2PO_4$ in a molar ratio between about 3:2 and about 2:3 to form a solid mixture, and grinding said solid mixture to produce said catalyst.

In another embodiment of the present invention, a method of preparing a catalyst is provided including the following steps: (a) combining $BaHPO_4$ and $KH_2PO_4$ in a molar ratio between about 3:2 and about 2:3 to form a solid mixture; (b) grinding said solid mixture to produce a mixed powder; (c) calcining said mixed powder at about 550° C. to produce a condensed phosphate mixture; and (d) contacting said condensed phosphate mixture with a gaseous mixture comprising water and lactic acid at a temperature of about 350° C. and a total pressure of about 25 bar to produce said catalyst, and wherein the partial pressure of water in said gaseous mixture is about 12.5 bar.

In another embodiment of the present invention, a method of preparing a catalyst is provided including the following steps: (a) combining $K_2HPO_4$, $Ba(NO_3)_2$, $H_3PO_4$, and water to form a wet mixture, wherein the molar ratio of $Ba(NO_3)_2$, $K_2HPO_4$, and $H_3PO_4$ is about 3:1:4; (b) heating said wet mixture to about 80° C. with stirring until near dryness to form a wet solid; (c) calcining said wet solid stepwise at about 50° C., about 80° C., about 120° C., and about 450° C. to about 550° C. to produce a dried solid; and (d) contacting said dried solid with a gaseous mixture comprising water and lactic acid at a temperature of about 350° C. and a total pressure of about 25 bar to produce said catalyst, and wherein the partial pressure of water in said gaseous mixture is about 12.5 bar.

Additional features of the invention may become apparent to those skilled in the art from a review of the following detailed description, taken in conjunction with the examples.

DETAILED DESCRIPTION OF THE INVENTION

I Definitions

As used herein, the term "monophosphate" or "orthophosphate" refers to any salt whose anionic entity, $[PO_4]^{3-}$, is composed of four oxygen atoms arranged in an almost regular tetrahedral array about a central phosphorus atom.

As used herein, the term "condensed phosphate" refers to any salts containing one or several P—O—P bonds generated by corner sharing of $PO_4$ tetrahedra.

As used herein, the term "polyphosphate" refers to any condensed phosphates containing linear P—O—P linkages by corner sharing of $PO_4$ tetrahedra leading to the formation of finite chains.

As used herein, the term "oligophosphate" refers to any polyphosphates that contain five or less $PO_4$ units.

As used herein, the term "cyclophosphate" refers to any cyclic condensed phosphate constituted of two or more corner-sharing $PO_4$ tetrahedra.

As used herein, the term "ultraphosphate" refers to any condensed phosphate where at least two $PO_4$ tetrahedra of the anionic entity share three of their corners with the adjacent ones.

As used herein, the term "cation" refers to any atom or group of covalently-bonded atoms having a positive charge.

As used herein, the term "anion" refers to any atom or group of covalently-bonded atoms having a negative charge.

As used herein, the term "monovalent cation" refers to any cation with a positive charge of +1.

As used herein, the term "polyvalent cation" refers to any cation with a positive charge equal or greater than +2.

As used herein, the term "heteropolyanion" refers to any anion with covalently bonded $XO_p$ and $YO_r$ polyhedra, and thus includes X—O—Y, and possibly X—O—X and Y—O—Y bonds, wherein X and Y represent any atoms, and wherein p and r are any positive integers.

As used herein, the term "heteropolyphosphate" refers to any heteropolyanion, wherein X represents phosphorus (P) and Y represents any other atom.

As used herein, the term "phosphate adduct" refers to any compound with one or more phosphate anions and one or more non-phosphate anions that are not covalently linked.

As used herein, the terms "LA" refers to lactic acid, "AA" refers to acrylic acid, "AcH" refers to acetaldehyde, and "PA" refers to propionic acid.

As used herein, the term "particle span" refers to a statistical representation of a given particle sample and is equal to $(D_{v,0.90}-D_{v,0.10})/D_{v,0.50}$. The term "median particle size" or $D_{v,0.50}$ refers to the diameter of a particle below which 50% of the total volume of particles lies. Further, $D_{v,0.10}$ refers to the particle size that separates the particle sample at the 10% by volume fraction and $D_{v,0.90}$, is the particle size that separates the particle sample at the 90% by volume fraction.

As used herein, the term "conversion" in % is defined as [hydroxypropionic acid, hydroxypropionic acid derivatives, or mixtures thereof flow rate in (mol/min)−hydroxypropionic acid, hydroxypropionic acid derivatives, or mixtures thereof flow rate out (mol/min)]/[hydroxypropionic acid, hydroxypropionic acid derivatives, or mixtures thereof flow rate in (mol/min)]*100. For the purposes of this invention, the term "conversion" means molar conversion, unless otherwise noted.

As used herein, the term "yield" in % is defined as [product flow rate out (mol/min)/hydroxypropionic acid, hydroxypropionic acid derivatives, or mixtures thereof flow rate in (mol/min)]*100. For the purposes of this invention, the term "yield" means molar yield, unless otherwise noted.

As used herein, the term "selectivity" in % is defined as [Yield/Conversion]*100. For the purposes of this invention, the term "selectivity" means molar selectivity, unless otherwise noted.

As used herein, the term "Gas Hourly Space Velocity" or "GHSV" in $h^{-1}$ is defined as 60×[Total gas flow rate (mL/min)/catalyst bed volume (mL)]. The total gas flow rate is calculated under Standard Temperature and Pressure conditions (STP; 0° C. and 1 atm).

As used herein, the term "Liquid Hourly Space Velocity" or "LHSV" in $h^{-1}$ is defined as 60×[Total liquid flow rate (mL/min)/catalyst bed volume (mL)].

II Catalysts

Unexpectedly, it has been found that catalysts containing mixed monophosphates anions dehydrate hydroxypropionic acid, hydroxypropionic acid derivatives, or mixtures thereof to acrylic acid, acrylic acid derivatives, or mixtures thereof with high: 1) yield and selectivity for acrylic acid, acrylic acid derivatives, or mixtures thereof, i.e., low amount and few side products; 2) efficiency, i.e., performance in short residence time; and 3) longevity. Although not wishing to be bound by any theory, applicants hypothesize that the catalyst, which includes at least monohydrogen monophosphate and dihydrogen monophosphate anions and two different cations, works as follows: the carboxylate group of the hydroxypropionic acid, hydroxypropionic acid derivatives, or mixtures thereof, associates with one or several cations, which in one embodiment is polyvalent, through one or both oxygen atoms, holding the molecule onto the surface of the catalyst, deactivating it from decarbonylation, and activating the C—OH bond for elimination. Then, the resulting protonated monophosphate anions dehydrate the hydroxypropionic acid, hydroxypropionic acid derivatives, or mixtures thereof by concerted protonation of the hydroxyl group, removal of a proton from the methyl group, and elimination of the protonated hydroxyl group as a molecule of water, generating acrylic acid, acrylic acid derivatives, or mixtures thereof and reactivating the catalyst. Furthermore, applicants believe that a specific protonation state of the monophosphate anions is important to facilitate the dehydration of hydroxypropionic acid, hydroxypropionic acid derivatives, or mixtures thereof.

In one embodiment, the catalyst includes: (a) monohydrogen monophosphate described by formula (I)

$$[HPO_4]^{2-} \tag{I},$$

(b) dihydrogen monophosphate anions described by formula (II):

$$[H_2PO_4]^- \tag{II},$$

and (c) at least two different cations, wherein the catalyst is essentially neutrally charged; and further, wherein the molar ratio of said monohydrogen monophosphate anion to said dihydrogen monophosphate anion in the catalyst is between about 0.1 and about 10. In another embodiment, the molar ratio of monohydrogen monophosphate anion to dihydrogen monophosphate anion is between about 0.2 and about 5. In yet another embodiment, the molar ratio of monohydrogen monophosphate anion to dihydrogen monophosphate anion is about 1.

In one embodiment of the present invention, the catalyst includes the monophosphate salts described by both the formulae (III) and (IV):

$$M^{II}HPO_4 \tag{III},$$

$$M^{I}H_2PO_4 \tag{IV}, and$$

wherein $M^I$ is a monovalent cation and $M^{II}$ is a divalent cation. In another embodiment, the molar ratio of $M^{II}HPO_4$ to $M^{I}H_2PO_4$ is between about 0.1 and about 10. In another embodiment, the molar ratio of $M^{II}HPO_4$ to $M^{I}H_2PO_4$ is between about 0.2 and about 5. In yet another embodiment, the molar ratio of $M^{II}HPO_4$ to $M^{I}H_2PO_4$ is about 1.

In one embodiment of the present invention, the catalyst includes a monophosphate salt described by the formula (V):

$$M^{II}_{2-x}M^{I}_{x}H_{x}(HPO_4)_2 \tag{V},$$

wherein $M^I$ is a monovalent cation and is a divalent cation; and wherein x is greater than about 0.2 and smaller than about 1.8. In another embodiment of the present invention, x is about 1.

In another embodiment, the monohydrogen monophosphate anion described by formula (I) is substituted by one or more phosphate anions described by the formula $[H_{(1-v)}P_{(1+v)}O_{(4+3v)}]^{2(1+v)-}$, wherein v is greater or equal to zero and less or equal to 1.

In another embodiment, the dihydrogen monophosphate anion described by formula (II) is substituted by one or more phosphate anions described by the formula $[H_{2(1-v)}PO_{4-v}]^-$, wherein v is greater or equal to zero and less or equal to 1.

In one embodiment, the at least two different cations comprise (a) at least one monovalent cation, and (b) at least one polyvalent cation. In another embodiment, the molar ratio of the monovalent cations to the polyvalent cations is between about 0.1 and about 10. In yet another embodiment, the molar ratio of the monovalent cations to the polyvalent cations is between about 0.5 and about 5. In a further embodiment of the present invention, the molar ratio of the monovalent cations to the polyvalent cations is about 1.

In one embodiment, the polyvalent cation is selected from the group consisting of divalent cations, trivalent cations, tetravalent cations, pentavalent cations, and mixtures thereof. Non-limiting examples of monovalent cations are $Li^+$, $Na^+$, $K^+$, $Rb^+$, $Cs^+$, $Ag^+$, $Rb^+$, $Tl^+$, and mixtures thereof. In one embodiment, the monovalent cation is selected from the group consisting of $Li^+$, $Na^+$, $K^+$, $Rb^+$, $Cs^+$, and mixtures thereof. In another embodiment, the monovalent cation is $Na^+$ or $K^+$; and in yet another embodiment, the monovalent cation is $K^+$. Non-limiting examples of polyvalent cations are cations of the alkaline earth metals (i.e., Be, Mg, Ca, Sr, Ba, and Ra), transition metals (e.g. Y, Ti, Zr, V, Nb, Cr, Mo, Mn, Re, Fe, Ru, Co, Rh, Ni, Pd, Pt, Cu, Ag, and Au), poor metals (e.g. Zn, Ga, Si, Ge, B, Al, In, Sb, Sn, Bi, and Pb), lanthanides (e.g. La and Ce), and actinides (e.g. Ac and Th). In one embodiment, the polyvalent cation is selected from the group consisting of $Be^{2+}$, $Mg^{2+}$, $Ca^{2+}$, $Sr^{2+}$, $Ba^{2+}$, $Mn^{2+}$, $Fe^{2+}$, $Co^{2+}$, $Ni^{2+}$, $Cu^{2+}$, $Zn^{2+}$, $Cd^{2+}$, $Sn^{2+}$, $Pb^{2+}$, $Ti^{3+}$, $Cr^{3+}$, $Mn^{3+}$, $Fe^{3+}$, $Al^{3+}$, $Ga^{3+}$, $Y^{3+}$, $In^{3+}$, $Sb^{3+}$, $Bi^{3+}$, $Si^{4+}$, $Ti^{4+}$, $V^{4+}$, $Ge^{4+}$, $Mo^{4+}$, $Pt^{4+}$, $V^{5+}$, $Nb^{5+}$, $Sb^{5+}$, and mixtures thereof. In one embodiment, the polyvalent cation is selected from the group consisting of $Ca^{2+}$, $Ba^{2+}$, $Cu^{2+}$, $Mn^{2+}$, $Mn^{3+}$, and mixtures thereof. In another embodiment, the polyvalent cation is selected from the group consisting of $Ca^{2+}$, $Ba^{2+}$, $Mn^{2+}$, and mixtures thereof. In yet another embodiment, the polyvalent cation is $Ba^{2+}$.

The catalyst can include cations: (a) $Li^+$, $Na^+$, $K^+$, $Rb^+$, $Cs^+$, or mixtures thereof; and (b) $Be^{2+}$, $Mg^{2+}$, $Ca^{2+}$, $Sr^{2+}$, $Ba^{2+}$, $Mn^{2+}$, $Fe^{2+}$, $Co^{2+}$, $Ni^{2+}$, $Cu^{2+}$, $Zn^{2+}$, $Cd^{2+}$, $Sn^{2+}$, $Pb^{2+}$, $Ti^{3+}$, $Cr^{3+}$, $Mn^{3+}$, $Fe^{3+}$, $Al^{3+}$, $Ga^{3+}$, $Y^{3+}$, $In^{3+}$, $Sb^{3+}$, $Bi^{3+}$, $Si^{4+}$, $Ti^{4+}$, $V^{4+}$, $Ge^{4+}$, $Mo^{4+}$, $Pt^{4+}$, $V^{5+}$, $Nb^{5+}$, $Sb^{5+}$, or mixtures thereof. In one embodiment the catalyst comprises $Li^+$, $Na^+$, or $K^+$ as monovalent cation, and $Ca^{2+}$, $Ba^{2+}$, $Mn^{2+}$, or $Mn^{3+}$ as polyvalent cation. In another embodiment, the catalyst comprises $K^+$ as monovalent cation, and $Ca^{2+}$, $Ba^{2+}$, or $Mn^{2+}$ as polyvalent cation. In yet another embodiment, the catalyst comprises $K^+$ as the monovalent cation and $Ba^{2+}$ as the polyvalent cation.

In one embodiment, the catalyst can include an inert support that is constructed of a material selected from the group consisting of silicates, aluminates, carbons, metal oxides, and mixtures thereof. Alternatively, the carrier is inert relative to the reaction mixture expected to contact the catalyst. In the context of the reactions expressly described herein, in one embodiment the carrier is a low surface area silica or zirconia. When present, the carrier represents an amount of about 5 wt % to about 98 wt %, based on the total weight of the catalyst. Generally, a catalyst that includes an inert support can be made by one of two exemplary methods: impregnation or co-precipitation. In the impregnation method, a suspension of the solid inert support is treated with a solution of a pre-catalyst, and the resulting material is then activated under conditions that will convert the pre-catalyst to a more active state. In the co-precipitation method, a homogenous solution of the catalyst ingredients is precipitated by the addition of additional ingredients.

III Catalyst Preparation Methods

In one embodiment of the present invention, the method of preparing the catalyst includes mixing at least two phosphorus-containing compounds, wherein each said compound is described by one of formulae (VI) to (XXV), or any of the hydrated forms of said formulae:

$$M^I_a(H_{3-a}PO_4) \quad (VI)$$

$$M^{II}_a(H_{3-a}PO_4)_2 \quad (VII)$$

$$M^{III}_a(H_{3-a}PO_4)_3 \quad (VIII)$$

$$M^{IV}_a(H_{3-a}PO_4)_4 \quad (IX)$$

$$M^{II}_b(OH)_c(PO_4)_d \quad (X)$$

$$M^{III}_e(OH)_f(PO_4)_g \quad (XI)$$

$$M^{II}M^IPO_4 \quad (XII)$$

$$M^{III}M^I_3(PO_4)_2 \quad (XIII)$$

$$M^{IV}_2M^I(PO_4)_3 \quad (XIV)$$

$$M^I_hH_{4-h}P_2O_7 \quad (XV)$$

$$M^{II}_iH_{(4-2i)}P_2O_7 \quad (XVI)$$

$$M^{IV}P_2O_7 \quad (XVII)$$

$$M^{III}M^IP_2O_7 \quad (XVIII)$$

$$M^I H_j(PO_3)_{(1+j)} \quad (XIX)$$

$$M^{II}H_j(PO_3)_{(2+j)} \quad (XX)$$

$$M^{III}H_j(PO_3)_{(3+j)} \quad (XXI)$$

$$M^{IV}H_j(PO_3)_{(4+j)} \quad (XXII)$$

$$M^{II}_kM^I_l(PO_3)_r \quad (XXIII)$$

$$M^{III}_qM^I_p(PO_3)_s \quad (XXIV)$$

$$P_2O_5 \quad (XXV)$$

wherein $M^I$ is a monovalent cation; wherein $M^{II}$ is a divalent cation; wherein $M^{III}$ is a trivalent cation; wherein $M^{IV}$ is a tetravalent cation; wherein a is 0, 1, 2, or 3; wherein h is 0, 1, 2, 3, or 4; wherein i is 0, 1, or 2; wherein j is 0 or any positive integer; and wherein b, c, d, e, f, g, k, l, m, n, p and q are any positive integers, such that the equations: $2b=c+3d$, $3e=f+3g$, $r=2k+l$, and $s=3q+p$ are satisfied. In another embodiment, the method of preparing the catalyst includes contacting the phosphorus-containing compounds after mixing, with a gaseous mixture comprising water.

In one embodiment, the catalyst is prepared by mixing one or more phosphorus-containing compound of formula (VI), wherein said a is equal to 1, and one or more phosphorus-containing compound of formula (VII), wherein said a is equal to 2. In another embodiment, the catalyst is prepared by mixing $KH_2PO_4$ with $BaHPO_4$ or $CaHPO_4$.

In another embodiment, the catalyst is prepared by the steps including: (a) mixing one or more phosphorus-containing compound of formula (VI), wherein said a is equal to 1, and one or more phosphorus-containing compound of formula (XVI), wherein said i is equal to 2; and (b) contacting the mixture of phosphorus-containing compounds with a gaseous mixture comprising water. In another embodiment, the phosphorus-containing compounds are $KH_2PO_4$ and $Ba_2P_2O_7$ or $Ca_2P_2O_7$.

In another embodiment, the catalyst is prepared by the steps including: (a) mixing one or more phosphorus-containing compounds of formula (VII), wherein said a is equal to 2, and one or more phosphorus-containing compound of formula (XIX), wherein said j is equal to 0; and (b) contacting the mixture of the phosphorus-containing compounds with a gaseous mixture comprising water. In another embodiment, the phosphorus-containing compounds are $(KPO_3)_w$ and $BaHPO_4$ or $CaHPO_4$; wherein w is an integer greater than 2.

In yet another embodiment, the catalyst is prepared by the steps including: (a) mixing one or more phosphorus-containing compound of formula (XVI), wherein said i is equal to 2, and one or more phosphorus-containing compound of formula (XIX), wherein said j is equal to 0, and (b) contacting the mixture of the phosphorus-containing compounds with a gaseous mixture comprising water. In another embodiment, the phosphorus-containing compounds are $(KPO_3)_w$ and $Ba_2P_2O_7$ or $Ca_2P_2O_7$; wherein w is an integer greater than 2.

In one embodiment of the present invention, the method of preparing the catalyst includes mixing and heating: (a) at least one phosphorus-containing compound, wherein each said compound is described by one of formulae (VI) to (XXV), or any of the hydrated forms of said formulae:

$$M^I_a(H_{3-a}PO_4) \tag{VI}$$

$$M^{II}_a(H_{3-a}PO_4)_2 \tag{VII}$$

$$M^{III}_a(H_{3-a}PO_4)_3 \tag{VIII}$$

$$M^{IV}_a(H_{3-a}PO_4)_4 \tag{IX}$$

$$M^{II}_b(OH)_c(PO_4)_d \tag{X}$$

$$M^{III}_e(OH)_f(PO_4)_g \tag{XI}$$

$$M^{II}M^IPO_4 \tag{XII}$$

$$M^{III}M^I_3(PO_4)_2 \tag{XIII}$$

$$M^{IV}_2M^I(PO_4)_3 \tag{XIV}$$

$$M^I_hH_{4-h}P_2O_7 \tag{XV}$$

$$M^{II}_iH_{(4-2i)}P_2O_7 \tag{XVI}$$

$$M^{IV}P_2O_7 \tag{XVII}$$

$$M^{III}M^IP_2O_7 \tag{XVIII}$$

$$M^IH_j(PO_3)_{(1+j)} \tag{XIX}$$

$$M^{II}H_j(PO_3)_{(2+j)} \tag{XX}$$

$$M^{III}H_j(PO_3)_{(3+j)} \tag{XXI}$$

$$M^{IV}H_j(PO_3)_{(4+j)} \tag{XXII}$$

$$M^{II}_kM^I_l(PO_3)_r \tag{XXIII}$$

$$M^{III}_qM^I_p(PO_3)_s \tag{XXIV}$$

$$P_2O_5 \tag{XXV}$$

wherein $M^I$ is a monovalent cation; wherein $M^{II}$ is a divalent cation; wherein $M^{III}$ is a trivalent cation; wherein $M^{IV}$ is a tetravalent cation; wherein a is 0, 1, 2, or 3; wherein h is 0, 1, 2, 3, or 4; wherein i is 0, 1, or 2; wherein j is 0 or any positive integer; and wherein b, c, d, e, f, g, k, l, m, n, p and q are any positive integers, such that the equations: $2b=c+3d$, $3e=f+3g$, $r=2k+l$, and $s=3q+p$ are satisfied; and (b) at least one non-phosphorus-containing compound selected from the group consisting of nitrate salts, carbonate salts, acetate salts, metal oxides, chloride salts, sulfate salts, and metal hydroxides, wherein each said compound is described by one of the formulae (XXVI) to (L), or any of the hydrated forms of said formulae:

$$M^INO_3 \tag{XXVI}$$

$$M^{II}(NO_3)_2 \tag{XXVII}$$

$$M^{III}(NO_3)_3 \tag{XXVIII}$$

$$M^I_2CO_3 \tag{XXIX}$$

$$M^{II}CO_3 \tag{XXX}$$

$$M^{III}_2(CO_3)_3 \tag{XXXI}$$

$$(CH_3COO)M^I \tag{XXXII}$$

$$(CH_3COO)_2M^{II} \tag{XXXIII}$$

$$(CH_3COO)_3M^{III} \tag{XXXIV}$$

$$(CH_3COO)_4M^{IV} \tag{XXXV}$$

$$M^I_2O \tag{XXXVI}$$

$$M^{II}O \tag{XXXVII}$$

$$M^{III}_2O_3 \tag{XXXVIII}$$

$$M^{IV}O_2 \tag{XXXIX}$$

$$M^ICl \tag{XL}$$

$$M^{II}Cl_2 \tag{XLI}$$

$$M^{III}Cl_3 \tag{XLII}$$

$$M^{IV}Cl_4 \tag{XLIII}$$

$$M^I_2SO_4 \tag{XLIV}$$

$$M^{II}SO_4 \tag{XLV}$$

$$M^{III}_2(SO_4)_3 \tag{XLVI}$$

$$M^{IV}(SO_4)_2 \tag{XLVII}$$

$$M^IOH \tag{XLVIII}$$

$$M^{II}(OH)_2 \tag{XLIX}$$

$$M^{III}(OH)_3 \tag{L}$$

In another embodiment, the non-phosphorus containing compounds can be selected from the group consisting of carboxylic acid-derived salts, halide salts, metal acetylacetonates, and metal alkoxides.

In another embodiment, the method of preparing the catalyst includes contacting the phosphorus-containing and the non-phosphorus-containing compounds after mixing, with a gaseous mixture comprising water.

In one embodiment, the catalyst is prepared by the steps including mixing and heating one or more phosphorus-containing compound of formula (VI), wherein said a is equal to 2, a phosphorus-containing compound of formula (VI), wherein said a is equal to 0 (i.e., phosphoric acid), and one or more nitrate salts of formula (XXVII). In another embodiment, the catalyst is prepared by mixing and heating $K_2HPO_4$, $H_3PO_4$, and $Ba(NO_3)_2$. In yet another embodiment, the catalyst is prepared by mixing and heating $K_2HPO_4$, $H_3PO_4$, and $Ca(NO_3)_2$. In further another embodiment, the catalyst is prepared by mixing and heating $K_2HPO_4$, $H_3PO_4$, and $Mn(NO_3)_2 \cdot 4H_2O$.

In one embodiment of the present invention, the method of preparing the catalyst includes contacting: (a) a gaseous mixture comprising water, with (b) a mixture of compounds containing at least one condensed phosphate anion selected from the group consisting of formulae (LI) to (LIII),

   (LI)

   (LII)

   (LIII)

wherein n is at least 2; wherein m is at least 1; wherein, said mixture of compounds is essentially neutrally charged; and further, wherein the molar ratio of phosphorus to the monovalent and polyvalent cations in the catalyst is between about 0.7 and about 1.7. In another embodiment, the molar ratio of phosphorus to the monovalent and polyvalent cations is about 1.

In yet another embodiment, the catalyst is prepared by the steps including contacting: (a) a gaseous mixture comprising water, with (b) a mixture of compounds containing a condensed phosphate salt selected from the group consisting of $Ba_{2-y-z}K_{2y}H_{2z}P_2O_7$, $Ca_{2-y-z}K_{2y}H_{2z}P_2O_7$, $Mn_{1-y-z}K_{1+3y}H_{3z}P_2O_7$, $Mn_{1-y-z}K_{2+2y}H_{2z}P_2O_7$, and mixtures thereof; and $(KPO_3)_w$; wherein y and z are greater or equal to 0 and less than about 0.5 and w is an integer greater than 2.

In one embodiment, the catalyst can include an inert support that is constructed of a material selected from the group consisting of silicates, aluminates, carbons, metal oxides, and mixtures thereof. Alternatively, the carrier is inert relative to the reaction mixture expected to contact the catalyst. In another embodiment, the method of preparing the catalyst can further include mixing an inert support with the catalyst before, during, or after the mixing of the phosphorus-containing compounds, wherein the inert support includes silicates, aluminates, carbons, metal oxides, and mixtures thereof. In yet another embodiment, the method of preparing the catalyst can further include mixing an inert support with the catalyst before, during, or after the mixing and heating of the phosphorus-containing compounds and the non-phosphorus-containing compounds, wherein the inert support includes silicates, aluminates, carbons, metal oxides, and mixtures thereof.

Mixing of the phosphorus-containing compounds or the phosphorus-containing and non-phosphorus-containing compounds of the catalyst can be performed by any method known to those skilled in the art, such as, by way of example and not limitation: solid mixing and co-precipitation. In the solid mixing method, the various components are physically mixed together with optional grinding using any method known to those skilled in the art, such as, by way of example and not limitation, shear, extensional, kneading, extrusion, and others. In the co-precipitation method, an aqueous solution or suspension of the various components, including one or more of the phosphate compounds, is prepared, followed by optional filtration and heating to remove solvents and volatile materials (e.g., water, nitric acid, carbon dioxide, ammonia, or acetic acid). The heating is typically done using any method known to those skilled in the art, such as, by way of example and not limitation, convection, conduction, radiation, microwave heating, and others.

Following mixing, the catalyst is, in one embodiment, ground and sieved to provide a more uniform product. The particle size distribution of the catalyst particles includes a particle span that, in one embodiment, is less than about 3; in another embodiment, the particle size distribution of the catalyst particles includes a particle span that is less than about 2; and in yet another embodiment, the particle size distribution of the catalyst particles includes a particle span that is less than about 1.5. In another embodiment of the invention, the catalyst is sieved to a median particle size of about 50 μm to about 500 μm. In another embodiment of the invention, the catalyst is sieved to a median particle size of about 100 μm to about 200 μm.

The catalyst can be utilized to catalyze several chemical reactions. Non-limiting examples of reactions are: dehydration of hydroxypropionic acid to acrylic acid (as described in further detail below), dehydration of glycerin to acrolein, dehydration of aliphatic alcohols to alkenes or olefins, dehydrogenation of aliphatic alcohols to ethers, other dehydrogenations, hydrolyses, alkylations, dealkylations, oxidations, disproportionations, esterifications, cyclizations, isomerizations, condensations, aromatizations, polymerizations, and other reactions that may be apparent to those having ordinary skill in the art.

In one embodiment of the present invention, the catalyst is prepared by the steps including combining $BaHPO_4$ and $KH_2PO_4$ in a molar ratio between about 3:2 and about 2:3 to form a solid mixture, and grinding said solid mixture to produce the catalyst.

In another embodiment of the present invention, the catalyst is prepared by the steps including: (a) combining $BaHPO_4$ and $KH_2PO_4$ in a molar ratio between about 3:2 and about 2:3 to form a solid mixture; (b) grinding said solid mixture to produce a mixed powder; (c) calcining said mixed powder at about 550° C. to produce a condensed phosphate mixture; and (d) contacting said condensed phosphate mixture with a gaseous mixture comprising water and lactic acid at a temperature of about 350° C. and a total pressure of about 25 bar to produce said catalyst, and wherein the partial pressure of water in said gaseous mixture is about 12.5 bar.

In yet another embodiment of the present invention, the catalyst is prepared by the steps including: (a) combining $K_2HPO_4$, $Ba(NO_3)_2$, $H_3PO_4$, and water to form a wet mixture, wherein the molar ratio of $Ba(NO_3)_2$, $K_2HPO_4$, and $H_3PO_4$ is about 3:1:4; (b) heating said wet mixture to about 80° C. with stirring until near dryness to form a wet solid; (c) calcining said wet solid stepwise at about 50° C., about 80° C., about 120° C., and about 450° C. to about 550° C. to produce a dried solid; and (d) contacting said dried solid with a gaseous mixture comprising water and lactic acid at a temperature of about 350° C. and a total pressure of about 25 bar to produce said catalyst, and wherein the partial pressure of water in said gaseous mixture is about 12.5 bar.

IV Methods of Producing Acrylic Acid, Acrylic Acid Derivatives, or Mixtures Thereof A method for dehydrating hydroxypropionic acid, hydroxypropionic acid derivatives, or mixtures thereof to acrylic acid, acrylic acid derivatives, or mixtures thereof is provided.

Alternative catalysts comprising anions selected from the group consisting of non-phosphorus-containing anions, heteropolyanions, and phosphate adducts, and at least two different cations, wherein the catalyst is essentially neutrally charged, can be utilized for dehydrating hydroxypropionic acid, hydroxypropionic acid derivatives, or mixtures thereof to acrylic acid, acrylic acid derivatives, or mixtures thereof. Non-limiting examples of non-phosphorus-containing anions are arsenates, condensed arsenates, nitrates, sulfates, borates, carbonates, chromates, vanadates, niobates, tantalates, selenates, and other monomeric oxoanions or polyoxoanions that may be apparent to those having ordinary skill in the art. Non-limiting examples of heteropolyanions are heteropolyphosphates, such as arsenatophosphates, phosphoaluminates, phosphoborates, phosphocromates, phosphomolybdates, phosphosilicates, phosphosulfates, phosphotungstates, and others that may be apparent to those having ordinary skill in the art. Non-limiting examples of phosphate adducts are adducts of phosphate anions with telluric acid, halides, borates, carbonates, nitrates, sulfates, chromates, silicates, oxalates, mixtures thereof, or others that may be apparent to those having ordinary skill in the art.

Hydroxypropionic acid can be 3-hydroxypropionic acid, 2-hydroxypropionic acid (also called, lactic acid), or mixtures thereof. In one embodiment, the hydroxypropionic acid is lactic acid. Derivatives of hydroxypropionic acid can be metal or ammonium salts of hydroxypropionic acid, alkyl esters of hydroxypropionic acid, hydroxypropionic acid oligomers, cyclic di-esters of hydroxypropionic acid, hydroxypropionic acid anhydride, or a mixture thereof. Non-limiting examples of metal salts of hydroxypropionic acid are sodium hydroxypropionate, potassium hydroxypropionate, and calcium hydroxypropionate. Non-limiting examples of alkyl esters of hydroxypropionic acid are methyl hydroxypropionate, ethyl hydroxypropionate, butyl hydroxypropionate, 2-ethylhexyl hydroxypropionate, or mixtures thereof. A non-limiting example of cyclic di-esters of hydroxypropionic acid is dilactide.

Acrylic acid derivatives can be metal or ammonium salts of acrylic acid, alkyl esters of acrylic acid, acrylic acid oligomers, or mixtures thereof. Non-limiting examples of metal salts of acrylic acid are sodium acrylate, potassium acrylate, and calcium acrylate. Non-limiting examples of alkyl esters of acrylic acid are methyl acrylate, ethyl acrylate, butyl acrylate, 2-ethylhexyl acrylate, or mixtures thereof.

The stream comprising hydroxypropionic acid, hydroxypropionic acid derivatives, or mixtures thereof can include a liquid stream and an inert gas (i.e., a gas otherwise inert to the reaction mixture under the conditions of the method) that can be separately or jointly fed into an evaporation vessel upstream of the catalyst reactor for the stream to become gaseous. The liquid stream can include the hydroxypropionic acid, hydroxypropionic acid derivatives, or mixtures thereof and a diluent. Non-limiting examples of the diluent are water, methanol, ethanol, acetone, C3 to C8 linear and branched alcohols, C5 to C8 linear and branched alkanes, ethyl acetate, non-volatile ethers (including diphenyl ether), and mixtures thereof. In one embodiment, the diluent comprises water. In another embodiment, the liquid stream comprises an aqueous solution of lactic acid or lactic acid derivatives selected from the group consisting of lactide, lactic acid oligomers, salts of lactic acid, and alkyl lactates. In one embodiment, the liquid stream includes from about 2 wt % to about 95 wt % lactic acid or lactic acid derivatives, based on the total weight of the liquid stream. In another embodiment, the liquid steam includes from about 5 wt % to about 50 wt % lactic acid or lactic acid derivatives, based on the total weight of the liquid stream. In another embodiment, the liquid stream includes from about 10 wt % to about 25 wt % lactic acid or lactic acid derivatives, based on the total weight of the liquid stream. In another embodiment, the liquid stream includes about 20 wt % lactic acid or lactic acid derivatives, based on the total weight of the liquid stream. In another embodiment, the liquid stream comprises an aqueous solution of lactic acid along with derivatives of lactic acid. In another embodiment, the liquid stream comprises less than about 30 wt % of lactic acid derivatives, based on the total weight of the liquid stream. In another embodiment, the liquid stream comprises less than about 10 wt % of lactic acid derivatives, based on the total weight of the liquid stream. In yet another embodiment, the liquid stream comprises less than about 5 wt % of lactic acid derivatives, based on the total weight of the liquid stream.

The inert gas is a gas that is otherwise inert to the reaction mixture under the conditions of the method. Non-limiting examples of the inert gas are nitrogen, air, helium, argon, carbon dioxide, carbon monoxide, steam, and mixtures thereof. In one embodiment, the inert gas is nitrogen.

The stream comprising hydroxypropionic acid, hydroxypropionic acid derivatives, or mixtures thereof can be in the form of a gaseous mixture when contacting the catalyst. In one embodiment, the concentration of hydroxypropionic acid, hydroxypropionic acid derivatives, or mixtures thereof based on the total moles of said stream (calculated under STP conditions) is from about 0.5 mol % to about 50 mol %. In another embodiment, the concentration of hydroxypropionic acid, hydroxypropionic acid derivatives, or mixtures thereof based on the total moles of said stream (calculated under STP conditions) is from about 1 mol % to about 10 mol %. In another embodiment, the concentration of hydroxypropionic acid, hydroxypropionic acid derivatives, or mixtures thereof based on the total moles of said stream (calculated under STP conditions) is between about 1.5 mol % to about 3.5 mol %. In yet another embodiment, the concentration of hydroxypropionic acid, hydroxypropionic acid derivatives, or mixtures thereof based on the total moles of said stream (calculated under STP conditions) is about 2.5 mol %.

In one embodiment, the temperature at which said stream comprising hydroxypropionic acid, hydroxypropionic acid derivatives, or mixtures thereof contacts the catalyst is between about 120° C. and about 700° C. In another embodiment, the temperature at which said stream comprising hydroxypropionic acid, hydroxypropionic acid derivatives, or mixtures thereof contacts the catalyst is between about 150° C. and about 500° C. In another embodiment, the temperature at which said stream comprising hydroxypropionic acid, hydroxypropionic acid derivatives, or mixtures thereof contacts the catalyst is between about 300° C. and about 450° C. In yet another embodiment, the temperature at which said stream comprising hydroxypropionic acid, hydroxypropionic acid derivatives, or mixtures thereof contacts the catalyst is between about 325° C. and about 400° C.

In one embodiment, the stream comprising hydroxypropionic acid, hydroxypropionic acid derivatives, or mixtures thereof contacts the catalyst at a GHSV between about 720 $h^{-1}$ and about 36,000 $h^{-1}$. In another embodiment, the stream comprising hydroxypropionic acid, hydroxypropionic acid derivatives, or mixtures thereof contacts the catalyst at a GHSV between about 1,800 $h^{-1}$ to about 7,200 $h^{-1}$. In another embodiment, the stream comprising hydroxypropionic acid, hydroxypropionic acid derivatives, or mixtures thereof contacts the catalyst at a GHSV about 3,600 $h^{-1}$.

In one embodiment, the stream comprising hydroxypropionic acid, hydroxypropionic acid derivatives, or mixtures thereof contacts the catalyst at a pressure between about 0 psig and about 550 psig. In another embodiment, the stream comprising hydroxypropionic acid, hydroxypropionic acid derivatives, or mixtures thereof contacts the catalyst at a pressure of about 360 psig.

In one embodiment the diluents comprises water and the partial pressure of water in the gaseous mixture is between about 10 psi and about 500 psi. In another embodiment, the partial pressure of water in the gaseous mixture is between about 15 psi and about 320 psi. In yet another embodiment, the partial pressure of water in the gaseous mixture is about 190 psi.

In one embodiment, the stream comprising hydroxypropionic acid, hydroxypropionic acid derivatives, or mixtures thereof contacts the catalyst in a reactor having an interior surface comprising material selected from the group consisting of quartz, borosilicate glass, silicon, hastelloy, inconel, manufactured sapphire, stainless steel, and mixtures thereof. In another embodiment, the stream comprising hydroxypropionic acid, hydroxypropionic acid derivatives, or mixtures thereof contacts the catalyst in a reactor having an interior surface comprising material selected from the group consisting of quartz or borosilicate glass. In another embodiment, the stream comprising hydroxypropionic acid, hydroxypropionic acid derivatives, or mixtures thereof contacts the catalyst in a reactor having an interior surface comprising borosilicate glass.

In one embodiment, the method includes contacting the catalyst with a gaseous mixture comprising hydroxypropionic acid, hydroxypropionic acid derivatives, or mixtures thereof under conditions sufficient to produce acrylic acid, acrylic acid derivatives, or mixtures thereof in a yield of at least 50%. In another embodiment, the method includes contacting the catalyst with a gaseous mixture comprising hydroxypropionic acid, hydroxypropionic acid derivatives, or mixtures thereof under conditions are sufficient to produce acrylic acid, acrylic acid derivatives, or mixtures thereof in a yield of at least about 70% In another embodiment, the method includes contacting the catalyst with a gaseous mixture comprising hydroxypropionic acid, hydroxypropionic acid derivatives, or mixtures thereof under conditions are sufficient to produce acrylic acid, acrylic acid derivatives, or mixtures thereof in a yield of at least about 80%. In another embodiment, the method conditions are sufficient to produce acrylic acid, acrylic acid derivatives, or mixtures thereof with a selectivity of at least about 50%. In another embodiment, the method conditions are sufficient to produce acrylic acid, acrylic acid derivatives, or mixtures thereof with a selectivity of at least about 70%. In another embodiment, the method conditions are sufficient to produce acrylic acid, acrylic acid derivatives, or mixtures thereof with a selectivity of at least about 80%. In another embodiment, the method conditions are sufficient to produce acrylic acid, acrylic acid derivatives, or mixtures thereof with propanoic acid as an impurity, wherein the propanoic acid selectivity is less than about 5%. In another embodiment, the method conditions are sufficient to produce acrylic acid, acrylic acid derivatives, or mixtures thereof with propanoic acid as an impurity, wherein the propanoic acid selectivity is less than about 1%. In another embodiment, the method conditions are sufficient to produce acrylic acid, acrylic acid derivatives, or mixtures thereof with a conversion of said hydroxypropionic acid, hydroxypropionic acid derivatives, or mixtures thereof of more than about 50%. In another embodiment, the method conditions are sufficient to produce acrylic acid, acrylic acid derivatives, or mixtures thereof with a conversion of said hydroxypropionic acid, hydroxypropionic acid derivatives, or mixtures thereof of more than about 80%.

Among the benefits attainable by the foregoing embodiments is the low yield of side products. In one embodiment, the conditions are sufficient to produce propionic acid in a yield of less than about 6% from lactic acid present in the gaseous mixture. In another embodiment, the conditions are sufficient to produce propionic acid in a yield of less than about 1%, from lactic acid present in the gaseous mixture. In one embodiment, the conditions are sufficient to produce each of acetic acid, pyruvic acid, 1,2-propanediol, and 2,3-pentanedione in a yield of less than about 2% from lactic acid present in the gaseous mixture. In another embodiment, the conditions are sufficient to produce each of acetic acid, pyruvic acid, 1,2-propanediol, and 2,3-pentanedione in a yield of less than about 0.5%, from lactic acid present in the gaseous mixture. In one embodiment, the conditions are sufficient to produce acetaldehyde in a yield of less than about 8% from lactic acid present in the gaseous mixture. In another embodiment, the conditions are sufficient to produce acetaldehyde in a yield of less than about 4% from lactic acid present in the gaseous mixture. In another embodiment, the conditions are sufficient to produce acetaldehyde in a yield of less than about 3%, from lactic acid present in the gaseous mixture. These yields are believed to be, heretofore, unattainably low. Yet, these benefits are indeed achievable as further evidenced in the Examples set out below.

A method for dehydrating glycerin to acrolein is provided. The method includes contacting a glycerin containing stream with a catalyst comprising: (a) monohydrogen monophosphate and dihydrogen monophosphate anions described by formulae (I) and (II):

$$[HPO_4]^{2-} \quad (I),$$

$$[H_2PO_4]^{-} \quad (II), \text{ and}$$

(b) at least two different cations, wherein the catalyst is essentially neutrally charged; and further, wherein the molar ratio of said monohydrogen monophosphate anion to said dihydrogen monophosphate anion in the catalyst is between about 0.1 and about 10, whereby acrolein is produced as a result of said glycerin being contacted with the catalyst. Acrolein is an intermediate which can be converted to acrylic acid using conditions similar to what are used today in the second oxidation step in the propylene to acrylic acid process.

V Examples

The following examples are provided to illustrate the invention, but are not intended to limit the scope thereof. Examples 1 through 3 describe the preparation of different mixed condensed phosphate catalysts in accordance with various embodiments described above.

Example 1

Catalyst Preparation:
Barium monohydrogen phosphate, $BaHPO_4$ (20 g, 85.7 mmol, Sigma-Aldrich Co., St. Louis, Mo.; catalog #31139) was combined with potassium dihydrogen phosphate, $KH_2PO_4$ (7.8 g, 57.1 mmol, Sigma-Aldrich Co., St. Louis, Mo.; catalog #60216). The mixture was ground using a mortar and pestle until a fine powder was obtained. The material was dried at 105° C. for 2 h using a gravity convection oven to produce the catalyst. Finally, the material was analyzed by X-ray diffraction (XRD), allowing the identification of $BaHPO_4$ and $KH_2PO_4$ as expected.
Catalyst Testing:
The catalyst was contacted with a gaseous mixture containing L-lactic acid (2.4 mol %), water (49.6 mol %), and nitrogen (48.0 mol %) using the reactor system described in Section VI. The reaction was performed at 350° C. and 360 psig, resulting in a partial pressure of water of 186 psi. The results are summarized in Table 1 in Section VII.

Example 2

Catalyst Preparation:
Barium monohydrogen phosphate, $BaHPO_4$ (20 g, 85.7 mmol, Sigma-Aldrich Co., St. Louis, Mo.; catalog #31139) was combined with potassium dihydrogen phosphate, $KH_2PO_4$ (7.8 g, 57.1 mmol, Sigma-Aldrich Co., St. Louis, Mo.; catalog #60216). The mixture was ground using a mortar and pestle until a fine powder was obtained. The material was calcined at 550° C. for 27 h using a gravity convection oven. After calcination, the material was left inside the oven until it cooled down by itself. Finally, the catalyst was ground and sieved to about 100 μm to about 200 μm. The material was analyzed by XRD allowing the identification of α-$Ba_2P_2O_7$ and $KPO_3$.

Catalyst Testing:
The catalyst was contacted with a gaseous mixture containing L-lactic acid (2.4 mol %), water (49.6 mol %), and nitrogen (48.0 mol %) using the reactor system described in Section VI. The reaction was performed at 350° C. and 360 psig, resulting in a partial pressure of water of 186 psi. The results are summarized in Table 1 in Section VII.

Example 3

Catalyst Preparation:
An aqueous solution of barium nitrate, $Ba(NO_3)_2$ (3414 mL of a 0.08 g/mL stock solution, 1.04 mol, 99.999%; Sigma-Aldrich Co., St. Louis, Mo.; catalog #202754), was added to solid dibasic potassium phosphate, $K_2HPO_4$ (60.7 g, 0.35 mol, ≥98%; Sigma-Aldrich Co., St. Louis, Mo.; catalog #P3786) at room temperature. Phosphoric acid, $H_3PO_4$ (98 mL of an 85 wt %, density=1.684 g/mL, 1.44 mol; Acros Organics, Geel, Belgium; catalog #295700010), was added to the slurry, providing a solution containing potassium ($K^+$, $M^I$) and barium ($Ba^{2+}$, $M^{II}$) cations. The final pH of the suspension was about 1.6. The acid-containing suspension was then dried slowly in a glass beaker at 80° C. using a heating plate while magnetically stirring the suspension until the liquid was evaporated and the material was almost completely dried. After evaporation, the material was transferred to a crushable ceramic. Heating was continued in a oven with air circulation (N30/80 HA; Nabertherm GmbH, Lilienthal, Germany) at 50° C. for 2 h, then at 80° C. for 10 h (0.5° C./min ramp), 120° C. for 2 hours (0.5° C./min ramp) to remove residual water followed by calcination at 450° C. for 4 hours (2° C./min ramp). After calcination, the material was left inside the oven until it cooled down by itself at a temperature below 100° C. before it was taken out of the oven. Finally, the catalyst was ground and sieved to about 100 μm to about 200 μm. The material was analyzed by XRD and energy dispersive spectroscopy coupled to scanning electron microscopy (EDS/SEM) allowing the identification of σ-$Ba_2P_2O_7$, α-$Ba_3P_4O_{13}$, $Ba(NO_3)_2$, $(KPO_3)_w$, and an additional phase presumably composed of a condensed phosphate with significant amounts of potassium and barium. Some incorporation of K within all the Ba-containing phases was also detected. The molar ratio between phosphorus (P) and the cations ($M^I$ and $M^{II}$) in the condensed phosphate salts identified by XRD was about 1 to about 1.3.
Catalyst Testing:
The catalyst was contacted with a gaseous mixture containing L-lactic acid (2.3 mol %), water (49.9 mol %), and nitrogen (47.8 mol %) using the reactor system described in Section VI. The reaction was performed at 350° C. and 360 psig, resulting in a partial pressure of water of 187 psi. The results are summarized in Table 1 in Section VII.

After the reaction was completed, the catalyst was cooled down to 236° C. while keeping the total pressure at 360 psig and flowing a gaseous mixture containing water (50.6 mol %) and nitrogen (49.4 mol %). Then, the temperature was decreased to 213° C. at a total pressure of 200 psig while flowing the same gaseous mixture, followed by additional cooling steps to 180° C. at a total pressure of 100 psig and 125° C. at a total pressure of 10 psig. After cooling, the catalyst was analyzed by XRD and EDS/SEM allowing the identification of $BaHPO_4$, a mixed phase with apparent chemical composition $Ba_{2-x}K_xH_x(HPO_4)_2$, and small amounts of $Ba(H_2PO_4)_2$ and $(KPO_3)_w$, wherein x is about 1 and w is an integer greater than 2.

VI Test Procedures

XRD: The wide-angle data (WAXS) were collected on a STADI-P transmission mode diffractometer (Stoe & Cie GmbH, Darmstadt, Germany). The generator was operated at 40 kV/40 mA, powering a copper anode long-fine-focus Cu x-ray tube. The diffractometer incorporates an incident-beam curved germanium-crystal monochromator, standard incident-beam slit system, and an image plate-position sensitive detector with an angular range of about 124° 2θ. Data were collected in transmission mode. Samples were gently ground by hand using a mortar & pestle to fine powder consistency, if necessary, before loading into the standard sample holder for the instrument. Crystalline phases were identified using the most current powder diffraction database (from ICDD) using the Search/Match routines in Jade (Materials Data, Inc. v9.4.2).

SEM/EDS: The dry powders were dispersed onto a double sided copper or carbon tape which had been mounted onto a metal scanning electron microscope (SEM) substrate. Each specimen was coated with Au/Pd for approximately 65-80 s using a Gatan Alto 2500 Cryo preparation chamber. SEM imaging & energy dispersive spectroscopy (EDS) mapping were performed using either a Hitachi S-4700 FE-SEM or Hitachi S-5200 in-lens FE-SEM (Hitachi Ltd., Tokyo, Japan) both equipped for EDS with Bruker XFlash 30 mm2 SDD detectors (Quantax 2000 system with 5030 detector; Bruker Corp., Billerica, Mass.). EDS mapping was performed using an accelerating voltage of 10 kV in Analysis probe current mode. All maps were generated using Bruker Esprit V1.9 software within the Hypermap module.

Reactor: A 13 inch (330 mm) long stainless steel glass lined tube (SGE Analytical Science Pty Ltd., Ringwood, Australia) with a 4.0 mm internal diameter (ID) was packed with glass wool (3 inch/76 mm bed length), topped by catalyst (1.6 cm$^3$ bed volume, 5 inch/127 mm bed length) to give an 2.55 cm$^3$ packed bed (8 inch/203 mm) and 1.6 cm$^3$ (5 inch/127 mm) of free space at the top of the reactor. The tube was placed inside an aluminum block and placed in a clam shell furnace series 3210 (Applied Test Systems, Butler, Pa.) such as the top of the packed bed was aligned with the top of the aluminum block. The reactor was set-up in a down-flow arrangement and was equipped with a Knauer Smartline 100 feed pump (Berlin, Germany), a Brooks 0254 gas flow controller (Hatfield, Pa.), a Brooks back pressure regulator, and a catch tank. The clam shell furnace was heated such that the reactor wall temperature was kept constant at about 350° C. during the course of the reaction. The reactor was supplied with separate liquid and gas feeds that were mixed together before reaching the catalyst bed. The gas feed was composed of molecular nitrogen ($N_2$) at about 360 psig and at a flow of 45 mL/min. The liquid feed was an aqueous solution of lactic acid (20 wt % L-lactic acid) and was fed at 0.045 mL/min, After flowing through the reactor, the gaseous mixture was cooled and the liquids were collected in the catch tank for analysis by off-line HPLC using an Agilent 1100 system (Santa Clara, Calif.) equipped with a diode array detector (DAD) and a Waters Atlantis T3 column (Catalog #186003748; Milford, Mass.) using methods generally known by those having ordinary skill in the art. The gaseous mixture was analyzed on-line by GC using an Agilent 7890 system (Santa Clara, Calif.) equipped with a FID detector and Varian CP-Para Bond Q column (Catalog #CP7351; Santa Clara, Calif.).

Reactor Feed: A solution (113.6 g) of biomass-derived lactic acid (88 wt %, Purac Corp., Lincolnshire, Ill.) was dissolved in distilled water (386.4 g) to provide a solution with an expected lactic acid concentration of 20 wt %. This solution was heated at 95° C. to 100° C. for 12-30 hours. The resulting mixture was cooled and analyzed by HPLC (described above) against known weight standards.

VII Results

Table 1 summarizes the catalytic parameters obtained with the different catalysts described in Section V.

TABLE 1

| Example # | Residence Time, (s) | Time on Stream, (min) | LA Conversion, (%) | AA Yield, (%) | AA Selectivity, (%) | CO Yield, (%) | $CO_2$ Yield, (%) |
|---|---|---|---|---|---|---|---|
| 1 | 1.4 | 172 | 93 ± 2 | 60 ± 2 | 64 ± 3 | 4 ± 0 | 3 ± 1 |
| 2 | 1.2 | 379 | 53 ± 3 | 39 ± 1 | 73 ± 2 | 3 ± 0 | 2 ± 0 |
| 3 | 1.0 | 328 | 90 ± 2 | 76 ± 1 | 85 ± 1 | 4 ± 1 | 3 ± 2 |

The foregoing description is given for clearness of understanding only, and no unnecessary limitations should be understood therefrom, as modifications within the scope of the invention may be apparent to those having ordinary skill in the art.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A catalyst comprising:
   a. monophosphate salt $KH_2PO_4$; and
   b. monophosphate salt $M^{II}HPO_4$;
   wherein $M^{II}$ is selected from the group consisting of Mg, Ca, Sr, and Ba; and further, wherein the molar ratio of said $M^{II}HPO_4$ to said $KH_2PO_4$ in said catalyst is between about 0.2 and about 5.

* * * * *